US010292666B2

(12) United States Patent
Liu

(10) Patent No.: US 10,292,666 B2
(45) Date of Patent: May 21, 2019

(54) TABLE AND IMAGING SYSTEM INCLUDING THE SAME

(71) Applicant: GE MEDICAL SYSTEMS GLOBAL TECHNOLOGY COMPANY, LLC, Waukesha, WI (US)

(72) Inventor: ChangHong Liu, Beijing (CN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 142 days.

(21) Appl. No.: 15/510,281

(22) PCT Filed: Sep. 11, 2015

(86) PCT No.: PCT/US2015/049562
§ 371 (c)(1),
(2) Date: Mar. 10, 2017

(87) PCT Pub. No.: WO2016/040728
PCT Pub. Date: Mar. 17, 2016

(65) Prior Publication Data
US 2017/0281100 A1    Oct. 5, 2017

(30) Foreign Application Priority Data
Sep. 12, 2014   (CN) .......................... 2014 1 0465738

(51) Int. Cl.
*A61B 6/04*       (2006.01)
*A61B 6/03*       (2006.01)
*A61B 6/00*       (2006.01)
(52) U.S. Cl.
CPC ............ *A61B 6/0407* (2013.01); *A61B 6/032* (2013.01); *A61B 6/037* (2013.01); *A61B 6/4417* (2013.01); *A61B 6/50* (2013.01); *A61B 6/0457* (2013.01)

(58) Field of Classification Search
CPC .......... A61B 6/04; A61B 6/0407; A61B 6/03; A61B 6/035; A61B 6/44
See application file for complete search history.

(56) References Cited

U.S. PATENT DOCUMENTS 4,475,072 A     10/1984   Schwehr et al.
6,298,506 B1 *  10/2001   Heinold ............... A61B 6/0442
                                                        378/209
(Continued)

FOREIGN PATENT DOCUMENTS

JP       2008-142353 A       6/2008

OTHER PUBLICATIONS

International Search Report and Written Opinion issued in connection with corresponding PCT Application No. PCT/US2015/049562 dated Jan. 11, 2016.

(Continued)

*Primary Examiner* — Thomas R Artman

(57) ABSTRACT

Embodiments of the present invention provide a supporting table and an imaging system including the supporting table. Said supporting table comprises: a supporting table body; a bracket provided on the supporting table body to be supported by the supporting table body and configured to bear a target object, wherein the bracket can move to protrude out of the supporting table body; a supporting roller, which can be detachably mounted between the supporting table body and the bracket to support the bracket relative to the supporting table body when the bracket moves. Accordingly, overhanging deformation of the bracket may be a voided or minimized by the support of the supporting roller.

10 Claims, 2 Drawing Sheets

(56) References Cited

U.S. PATENT DOCUMENTS

2004/0261177 A1  12/2004  Hoth et al.
2008/0201849 A1   8/2008  Van Es et al.
2017/0281100 A1*  10/2017  Liu ........................ A61B 6/032

OTHER PUBLICATIONS

International Preliminary Report on Patentability issued in connection with corresponding PCT Application No. PCT/US2015/049562 dated Mar. 14, 2017.

* cited by examiner

TABLE AND IMAGING SYSTEM INCLUDING THE SAME

BACKGROUND

Embodiments of the present invention relate to a supporting table and an imaging system including the supporting table.

An imaging system, e.g., a medical imaging system, may include a supporting table for supporting a target object to be imaged and a scanning device for scanning the target object to obtain an image of the target object. Such imaging system may include a computerized tomography (CT) system, a magnetic resonance imaging (MRI) system, a single photon emission computerized tomography (SPECT) system.

The supporting table may usually include a bracket for bearing the target object to be imaged and a supporting table body for supporting the bracket. The bracket may move relative to the supporting table body, to move the target object born by the bracket to a specific scanning position to be scanned and imaged.

When a part of the bracket moves out of the supporting table body, it may not be supported by the supporting table body, therefore, an overhanging deformation may occur due to a gravity of this part itself and a gravity of the target object born by this part. Accordingly, it is possible that such bracket cannot be used in the imaging system such as a tumor-diagnosing scanning mode, because such scanning mode requires that the bracket remains no overhanging deformation or very little overhanging deformation.

SUMMARY OF THE INVENTION

An objective of exemplary embodiments of the present invention is to overcome the aforementioned and/or other problems in the prior art. Therefore, exemplary embodiments of the present invention provide a supporting table including a detachable supporting roller and an imaging system including the supporting table.

According to an exemplary embodiment, a supporting table comprises: a supporting table body; a bracket provided on the supporting table body to be supported by the supporting table body and configured to bear a target object, wherein the bracket can move to protrude out of the supporting table body; a supporting roller, which can be detachably mounted between the supporting table body and the bracket to support the bracket relative to the supporting table body when the bracket moves.

According to another exemplary embodiment, an imaging system comprises: the supporting table as described above, which is configured to bear a target object; a scanning device configured to scan the target object born by the supporting table to obtain an image of the target object, wherein when the scanning device scans in a first scanning mode, the supporting roller is mounted between the supporting table body and the bracket such that the bracket moves the target object to a scanning position in case of being supported by the supporting roller, and when the scanning device scans in a second scanning mode different from the first scanning mode, the supporting roller is detached from the supporting table body and the bracket such that the bracket moves the target object to the scanning position in case of not being supported by the supporting roller.

Other features and aspects will become apparent from the detailed description, the accompanying drawings and claims that follow.

BRIEF DESCRIPTION OF THE DRAWINGS

The present invention can be understood better in light of the description of exemplary embodiments of the present invention with reference to the accompanying drawings, in which.

DETAILED DESCRIPTION

Hereafter, a detailed description will be given for embodiments of the present invention. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art relating to the contents disclosed in the present invention, which should not be regarded as insufficient disclosure of the present invention.

Unless defined otherwise, all the technical or scientific terms used in the Claims and the Description should have the same meanings as commonly understood by one of ordinary skilled in the art to which the present invention belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
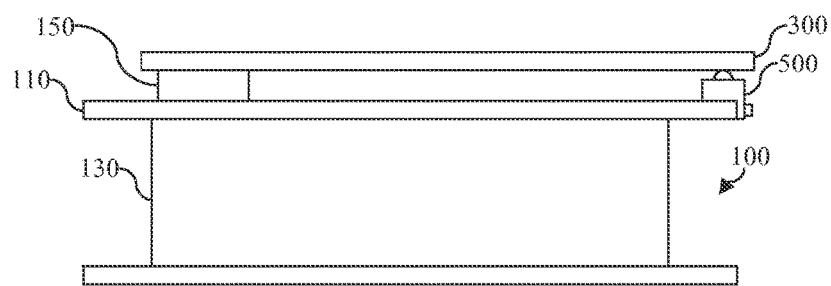
FIG. 1 is a diagram schematically illustrating a supporting table according to an exemplary embodiment.

FIG. 1 is a diagram schematically illustrating a supporting table according to an exemplary embodiment.

As shown in FIG. 1, the supporting table according to the exemplary embodiment may include a supporting table body 100, a bracket 300 and a supporting roller 500.

The supporting table body 100 may support the bracket 300. In an exemplary embodiment, the supporting table body 100 may include a lifting mechanism to adjust the bracket 300 to an appropriate height. For example, the supporting table body 100 may include a supporting platen 110, a base 130 and a bracket driving unit 150. The lifting mechanism may be included in the base 130 such that the base 130 may elevatably support the supporting platen 110. The bracket driving unit 150 may be provided on the supporting platen. As shown in FIG. 1, the bracket driving unit 150 may he integrated to an end of the bracket 300 to drive the bracket 300 to move.

The bracket 300 is provided on the supporting table body 100 and supported by the supporting table body 100. The bracket 300 may be used to bear a target object. For example, according to an exemplary embodiment, the bracket 300 may be used to bear a target object to be imaged (e.g., a user to be diagnosed) when the supporting table is applied to a medical imaging device such as a CT device, etc.

The bracket 300 may move relative to the supporting table body 100, e.g., move along a length direction of the supporting table body 100. In this way, the bracket 300 may move the target object born by the bracket 300 to a predetermined position. Herein, the predetermined position may be a scanning position at which the target object is scanned and imaged by the medical imaging device. For example, the bracket 300 may move to protrude out of the supporting table body 100, to move the target object born by the bracket 300 to a scanning position out of the supporting table body 100.

The supporting roller 500 may be detachably mounted between the supporting table body 100 and the bracket 300. In this way, when the bracket 300 moves, the supporting roller 500 mounted between the supporting table body 100 and the bracket 300 may support the bracket 300 relative to the supporting table body 100. As shown in FIG. 1, the supporting roller 500 may be mounted on an end portion of the supporting platen 110 corresponding to one end of the bracket 300 that would protrude out of the supporting table body 100. For example, the supporting roller 500 mounted on the end of the supporting platen 110 may be located to correspond to a middle of the bracket 100 and to contact with a bottom of the bracket 100. However, exemplary embodiments are not limited thereto. In other exemplary embodiments, multiple supporting rollers 500 may be mounted on the end portion of the supporting platen 110 to more evenly support the bracket 100.

Figure 2:
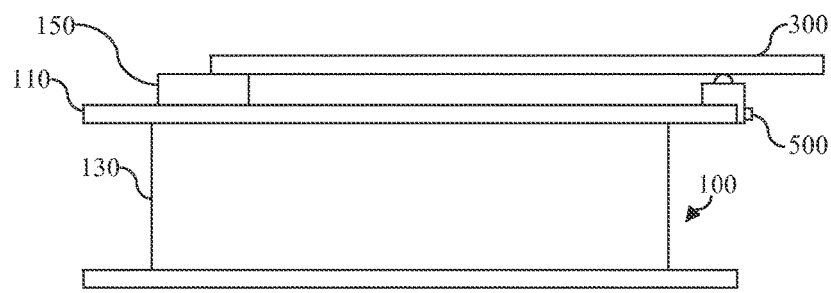
FIG. 2 is a diagram illustrating a state in which a bracket of the supporting table of FIG. 1 moves to a scanning position, wherein a supporting roller is mounted between a supporting table body and the bracket.
Figure 3:
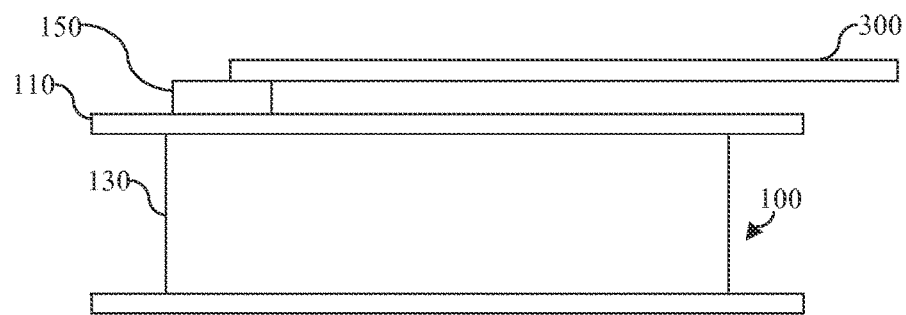
FIG. 3 is a diagram illustrating a state in which the bracket of the supporting table of FIG. 1 moves to the scanning position, wherein no supporting roller is mounted between the supporting table body and the bracket.

FIG. 2 is a diagram illustrating a state in which the bracket of the supporting table of FIG. 1 moves to a scanning position, wherein the supporting roller is mounted between the supporting table body and the bracket; FIG. 3 is a diagram illustrating a state in which the bracket of the supporting table of FIG. 1 moves to a scanning position, wherein no supporting roller is mounted between the supporting table body and the bracket.

As shown in FIG. 2. and FIG. 3, when the supporting roller 500 is mounted, an overhanging deformation of e.g., the bracket 300 moving out of the supporting table body 100 due to the gravity of the bracket 300 itself and the gravity of the target object born by the bracket 300 may be avoided or such overhanging deformation may be minimized Therefore, the supporting table according to the exemplary embodiment may be used in an imaging system with multiple scanning modes, which will be described in more details below.

Figure 4:
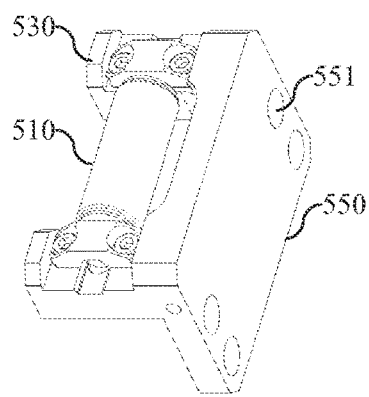
FIG. 4 is a perspective diagram illustrating a supporting roller according to an exemplary embodiment.

FIG. 4 is a perspective diagram illustrating a supporting roller according to an exemplary embodiment.

As shown in FIG. 4, the supporting roller 500 may include a roller body 510, a roller supporter 530 and a mounting part 550.

The roller body 510 may be provided on the roller supporter 550, and may be supported by the roller supporter 550. The roller body 510 may contact the bottom of the bracket 300, and may rotate along a direction in which the bracket 300 moves while the bracket 300 is moving.

The roller supporter 530 may he provided between the supporting platen 110 and the bracket 300 to support the bracket 300 relative to the supporting platen 110.

The mounting part 550 may extend from the roller supporter 530. The mounting part 500 may be detachably mounted on the end portion of the supporting platen 110. To this end, in one exemplary embodiment, the mounting part 550 may include a fixing member 551, such that the mounting part 550 may be fixed to the end portion of the supporting platen 110 by the fixing member. For example, the fixing member 551 may he a screw, The mounting part 550 may be integrally formed with the roller supporter 530, as shown in FIG. 4. However, the exemplary embodiments are not limited thereto. In other exemplary embodiments, the mounting part 550 may be connected to the roller supporter 530 by a connecting member. In this way, manufacturers may adjust the positions of the roller supporter 530 and the roller body 510 supported thereby when the supporting roller is mounted on the supporting platen 110 by the mounting part 550 according to different design requirements.

As mentioned above, a supporting table may be applied in an imaging system. The imaging system according to such exemplary embodiment may include a supporting table to bear the target object, and may further include a scanning device for scanning the target object born by the supporting table to obtain an image of the target object. The imaging system may have different scanning modes, which may include a first scanning mode in which the bracket of the supporting table is required to have no overhanging deformation or to have very little overhanging deformation, and a second scanning mode in which the bracket is allowed to have an overhanging deformation of some extent. For example, the imaging system may be an SPECT/CT hybrid imaging system, and the first scanning mode may be a tumor-diagnosing scanning mode in which the bracket of the supporting table is required to have no overhanging deformation or to have very little overhanging deformation.

Therefore, when the scanning device scans in the first scanning mode, the supporting roller may be mounted between the supporting table body and the bracket such that the bracket moves the target object to a scanning position in case of being supported by the supporting roller. In this way, an overhanging deformation of the bracket may be avoided or minimized by the supporting roller. On the other hand, when the scanning device scans in the second scanning mode, the supporting roller may be detached from the supporting table body and the bracket, such that the bracket moves the target object to the scanning position in case of not being supported by the supporting roller.

The supporting table and the imaging system according to the exemplary embodiments may include the detachable supporting roller, such that the bracket is supported while the bracket is moving relative to the supporting platen. Therefore, the overhanging deformation of the bracket may be avoided or minimized. Moreover, the supporting table and the imaging system according to the exemplary embodiments may be operated in different scanning modes by mounting and/or detaching the supporting roller, thus needing no replacement for the supporting table due to different scanning modes. Accordingly the cost of the imaging system may be saved, the operation of the imaging system may be simplified, and the scanning efficiency of the imaging system may be improved.

Some exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. Accordingly, other embodiments are also falling within the protection scope of the claims.

What is claimed is:

1. An imaging system, comprising:
   a supporting table comprising:
      a supporting table body;
      a bracket provided on the supporting table body to be supported by the supporting table body and configured to bear a target object, wherein the bracket is configured to move to protrude out of the supporting table body; and
      a plurality of supporting rollers detachably mounted between the supporting table body and the bracket to support the bracket relative to the supporting table body when the bracket moves; and
   a scanning device configured to scan the target object born by the supporting table to obtain an image of the target object,
   wherein when the scanning device scans in a first scanning mode, the plurality of supporting rollers is mounted between the supporting table body and the bracket such that the bracket moves the target object to a scanning position in case of being supported by the plurality of supporting rollers, and when the scanning device scans in a second scanning mode different from the first scanning mode, the plurality of supporting rollers is detached from the supporting table body and the bracket such that the bracket moves the target object to the scanning position in case of not being supported by the plurality of supporting rollers.

2. The imaging system according to claim 1, wherein said supporting table body comprises:
   a supporting platen;
   a base configured to be capable of elevatably supporting the supporting platen; and
   a bracket driving unit provided on the supporting platen and configured to drive the bracket to move.

3. The imaging system according to claim 1, wherein the plurality of rollers are mounted on an end portion of the supporting platen.

4. An imaging system, comprising:
   a supporting table comprising:
      a supporting table body;
      a bracket provided on the supporting table body to be supported by the supporting table body and configured to bear a target object, wherein the bracket is configured to move to protrude out of the supporting table body; and
      a supporting roller detachably mounted between the supporting table body and the bracket to support the bracket relative to the supporting table body when the bracket moves; and
   a scanning device configured to scan the target object born by the supporting table to obtain an image of the target object,
   wherein when the scanning device scans in a first scanning mode, the supporting roller is mounted between the supporting table body and the bracket such that the bracket moves the target object to a scanning position in case of being supported by the supporting roller, and when the scanning device scans in a second scanning mode different from the first scanning mode, the supporting roller is detached from the supporting table body and the bracket such that the bracket moves the target object to the scanning position in case of not being supported by the supporting roller.

5. The imaging system according to claim 4, wherein said supporting table body comprises:
   a supporting platen;
   a base configured to be capable of elevatably supporting the supporting platen; and
   a bracket driving unit provided on the supporting platen and configured to drive the bracket to move.

6. The imaging system according to claim 5, wherein the bracket driving unit is configured to be integrated to an end of the bracket, and the supporting roller is configured to be capable of being detachably mounted on an end portion of the supporting platen corresponding to another end of the bracket which will protrude out of the supporting table body.

7. The imaging system according to claim 6, wherein the supporting roller mounted on the end portion of the supporting platen is located to correspond to a middle of the bracket.

8. The imaging system according to claim 5, wherein the supporting roller comprises:
   a roller body;
   a roller supporter provided between the supporting platen and the bracket and configured to support the roller body; and
   a mounting part extending from the roller supporter and configured to be capable of being detachably mounted on an end portion of the supporting platen.

9. The imaging system according to claim 8, wherein the mounting part comprises:
   a fixing member configured to fix the mounting part to the end portion of the supporting platen.

10. The imaging system according to claim 4, wherein said imaging system is a single photon emission computerized tomography/computerized tomography hybrid imaging system, and the first scanning mode is a tumor-diagnosing scanning mode.

* * * * *